United States Patent

Schönartz

Patent Number: 5,438,603
Date of Patent: Aug. 1, 1995

[54] DEVICE FOR RADIOGRAPHY WITHOUT THE USE OF FILM

[75] Inventor: Norbert Schönartz, Mettmann, Germany

[73] Assignee: Mannesmann Aktiengesellschaft, Dusseldorf, Germany

[21] Appl. No.: 186,304

[22] Filed: Jan. 25, 1994

[30] Foreign Application Priority Data

Jan. 25, 1993 [DE] Germany ............... 43 02 286.3

[51] Int. Cl.⁶ .............................................. G01B 15/06
[52] U.S. Cl. .................................. 378/39; 378/194
[58] Field of Search ............................. 378/59, 194

[56] References Cited

U.S. PATENT DOCUMENTS 4,078,180 3/1978 Green .................................. 378/59

Primary Examiner—Craig E. Church
Attorney, Agent, or Firm—Cohen, Pontani, Lieberman & Pavane

[57] ABSTRACT

A radiographic device for testing the welds of elongate, welded hollow bodies of metal without the use of film includes a liquid-cooled X-ray tube movable axially within the hollow body being tested and an X-ray image converter situated in the region irradiated by the X-ray tube. A high-voltage generator is fastened to a displaceable holder carriage for movement in directions parallel or vertical to the longitudinal axis of the hollow body being tested. At least one high-voltage cable is connected, via guide rollers arranged outside the hollow body being tested. The length of the cable is dimensioned to enable a displacement of the X-ray tube from one end to the other for the longest hollow body to be tested. Concrete shielding need only be slightly longer than the longest hollow body to be tested.

14 Claims, 1 Drawing Sheet

DEVICE FOR RADIOGRAPHY WITHOUT THE USE OF FILM

BACKGROUND OF THE INVENTION

1. Field of the Invention

The invention is directed to a device for radiographically testing the weld of elongate, welded hollow bodies of metal, in particular steel pipes, without the use of film.

1. Discussion of Prior Art

In X-ray testing of the weld of elongate, welded hollow bodies of metal, aside from the classic method using film, there is also a growing interest in non-film methods which make use of image converters. In this method, the X-rays penetrating the seam of the hollow body in the direction of thickness impinge on a radiation-sensitive sensor which converts the occurring radiation energy into electric signals which are then processed in a computer. In so doing, it is unimportant from the point of view of the actual measurement process whether the liquid-cooled X-ray tube is arranged inside or outside the hollow body. In hollow bodies of smaller dimensions, i.e. less than approximately 600 mm clear width, this freedom of choice no longer exists, since an image converter having a cross section of substantially greater dimensions than the X-ray tube could no longer be accommodated inside the hollow body. Moreover, because of the curvature of the pipe wall in the case of a pipe, there is always a minimum distance between the input screen of the image converter and the weld to be tested which is determined by the pipe radius and the geometry of the X-ray image converter. A geometrical blurring which impairs the quality of the image can result due to the finite magnitude of the focal spot of the X-ray tube.

The fundamental standards for acceptance tests of welded steel piping, particularly large pipes, dictate that both end regions of the pipe be tested in a length of at least 200 mm. Moreover, all weld seams for which readings were obtained in prior ultrasonic testing must be checked by means of X-ray. This means that every portion of the entire weld length must be capable of testing, which necessitates a corresponding displacement of the X-ray tube relative to the hollow body.

In stationary X-ray tubes the hollow body must be moved axially. This is a disadvantage as the concrete shielding must then have a length at least twice that of the longest hollow body to be tested. This is also the case when the X-ray tube is moved, since the high-voltage generator having large cross-sectional dimensions cannot be inserted into the pipe along with the X-ray tube and the high-voltage cable or, in the case of a two-pole X-ray tube, the high-voltage cables and the other supply lines between the high-voltage generator and X-ray tube must be at least twice as long as the longest hollow body to be tested. When the hollow body has a length of more than 12 m, such an arrangement cannot be used regardless of the cost of a longer concrete shielding, since the length of the high-voltage cable is limited to approximately 25 mm for reasons pertaining to load. A possible solution with respect to a short length of the concrete shield would be to wind the high-voltage cable and other supply lines on to a large drum, wherein the high-voltage generator would also have to be rotated. Such winding would mean a high mechanical loading of the thick and inflexible high-voltage cable. Moreover, the rotation of the generator would cause problems with the connections of the control lines and supply lines. Difficulties would also arise with regard to the coolant supply and the system would be highly prone to disturbance.

It is therefore an object of the present invention to provide a device for radiographically testing, without film, the weld of elongate, welded hollow bodies such as steel pipes which is not susceptible to disturbances.

It is a further object of the present invention to provide a testing device suitable for use with hollow bodies having a small clear width and lengths of more than 12 m.

It is yet another object of the present invention to provide a testing device for which a concrete shield only slightly longer than the longest hollow body to be tested is adequate.

SUMMARY OF THE INVENTION

The aforementioned objects, as well as other advantages and benefits which will be apparent to those skilled in the art, are achieved by a device which comprises a liquid cooled X-ray tube positionable within an elongate, welded, hollow body of metal for displacement along the length thereof, a high-voltage generator displaceable relative to the first and second ends of the hollow body in response to movement of the X-ray tube, connecting means interconnecting the high voltage generator to the x-ray tube and including at least one cable of sufficient length to enable displacement of said X-ray tube from the first end to the second end of the hollow body, and an X-ray image converter adapted for synchronous movement with the X-ray tube, wherein the image converter is always positioned in a region irradiated by the X-ray tube.

The advantage of the proposed device consists in that radiography without the use of film can also be applied for hollow bodies having a small clear width, i.e. less than approximately 600 mm, without requiring a longer concrete shield.

In the illustrative embodiment, a carriage carrying the high-voltage generator moves is movable on rails preferably arranged above the hollow body. A roller bed or roller track for the tested pipe is preferably arranged on the floor of the concrete shield, which shield is usually constructed as a bunker installation. However, there is sufficient headroom to accommodate the movable carriage above the hollow body without difficulty. The X-ray image converter must also be arranged so as to be displaceable synchronously with the X-ray tube so as to remain in position relative thereto. The high-voltage cable and a line for cooling the X-ray tube are preferably guided by respective pairs of deflecting rollers.

The diameters of the deflecting rollers are so dimensioned that no impermissible bending stresses occur on the sensitive high-voltage cable. This is also true of the cross-sectional configuration of the rollers, so that the cable can conform without kinking. Due to the opposed movement of the carriage and X-ray tube, the high-voltage cable is always subject to the same tension and the maximum length of cable is guided in a straight manner. In the case of pipe testing, the configuration in which the X-ray tube is arranged inside also enables better testing conditions in general.

BRIEF DESCRIPTION OF THE DRAWINGS

The device according to the invention is explained in more detail in the drawing, which shows a basic diagram of the device according to the invention.

DETAILED DESCRIPTION OF THE PREFERRED EMBODIMENTS

Figure 1:
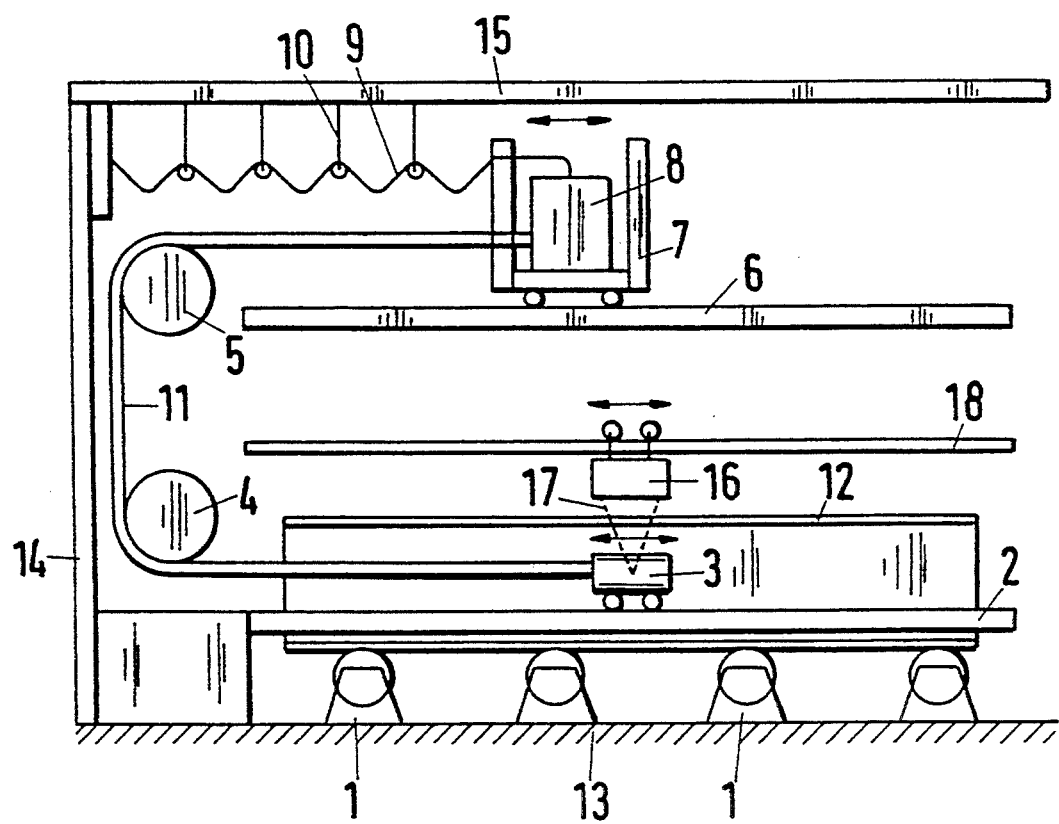

The hollow body to be tested, in this example a pipe 12, is moved into a fixed test position on a longitudinal roller track having a plurality of rollers 1 and is arranged on the floor 13 of an X-ray device. Transverse rotating rollers (not shown) may be utilized to bring the pipe into the required angular position, e.g. a 12 o'clock position. The installation is conventionally shielded by concrete walls 14, 15, only the left end and upper shield being shown in the drawing for clarity. A stationary crossbeam 2, on which the X-ray tube 3 is linearly displaceable, projects into the test pipe 12 in an axial direction. A double arrow represents the directions in which X-ray tube 3 may be moved. The length of the crossbeam 2 is longer than the longest hollow body to be tested so that the X-ray tube 3 can be moved continuously to every longitudinal position of the pipe 12.

For the sake of simplicity, the drawing shows only one of the supply lines of the X-ray tube 3, a high-voltage cable 11 which is coupled to high-voltage generator mounted on a carriage 7. As will be described in more detail later, the supply lines as cable 11 are supported by guide means such as deflecting rollers 4 and 5. The carriage 7 is arranged so as to be displaceable on a guide rail 6, this displacement possibility being represented by a double arrow. In the illustrative embodiment depicted in the FIGURE, the guide rail lies above and parallel to the longitudinal axis of the hollow body to be tested. Alternatively, depending on the available space, guide rail 6 may be arranged in a cellar space below the hollow body. For lateral guidance of the cable 11, it is also conceivable to arrange the guide rail vertical to the longitudinal axis of the hollow body.

Preferably, and as shown in the FIGURE, carriage 7 is moved opposite to the direction of displacement of the X-ray tube 3 so that the same tension is always applied to the cable 11. Further, the majority of the length of the cable is guided in a straight manner so that mechanical loading is slight. Such guiding is further enhanced by selecting the diameters of rollers 4 and 5 so that no unacceptable bending stresses occur on the side of the cable or cables contacting them. Suitable constructions of the cable connections to the X-ray tube 3 and high-voltage generator 8 and of the crossbeam 2 and guide rail 6 ensure a minimum sagging of the cable 11 between the lower deflecting roller 4 and the X-ray tube 3 and between the upper deflecting roller 5 and the high-voltage generator 8.

It will be readily appreciated that such auxiliary devices as may be required for operating the X-ray tube 3, e.g. pressure regulators for the coolant, may be mounted on carriage 7, if desired. The control lines and supply lines 9 may be fed to carriage 7 in a known manner via a cable hauling device 10 or the like.

To carry out radiography without the use of film, an X-ray image converter 16 is arranged outside the hollow body and is moved synchronously with the X-ray tube 3 so that the X-rays 17 indicated in the drawing always impinge on the sensor arranged in the X-ray image converter 16. As shown in the FIGURE, the X-ray image converter 16 is likewise guided on a crossbeam 18 so as to be displaceable as indicated by the double arrow. The selection of means for synchronously moving image converter 16 and X-ray tube 3 is not deemed to constitute a novel aspect of the present invention. Accordingly, any suitable means for simultaneously moving the x-ray tube 3 and image converter 16 along their respective crossbeams may be employed. By way of example, the x-ray tube 3 and image converter 16, which are positioned on wheeled assemblies as shown, may be advanced by suitable, commonly connected pulling cables (not shown).

The invention is not limited by the embodiments described above which are presented as examples only but can be modified in various ways within the scope of protection defined by the appended patent claims.

What is claimed is:

1. A device for testing the welds of elongate, welded hollow metal bodies, each hollow body to be tested having a first end and a second end, comprising:

an X-ray tube positionable within a hollow body to be tested for displacement from the first end to the second end;

a high-voltage generator displaceable relative to the first and second ends in response to movement of said X-ray tube;

connecting means interconnecting said high voltage generator to said x-ray tube, said connecting means including at least one cable of sufficient length to enable displacement of said X-ray tube from the first end to the second end; and an X-ray image converter adapted for synchronous movement with said X-ray tube, wherein said image converter is always positioned in a region irradiated by the X-ray tube.

2. A device according to claim 1, further comprising rails and a carriage movable on said rails, wherein said high voltage generator is disposed on said carriage.

3. A device according to claim 2, wherein said rails are disposed above the hollow body to be tested.

4. A device according to claim 1, wherein said connecting means further includes guide means for supporting said at least one cable.

5. A device according to claim 4, wherein said guide means include first and second rollers.

6. A device according to claim 1, wherein said x-ray tube is disposed on a movable carriage.

7. A device according to claim 1, wherein said image converter is disposed on a movable carriage.

8. A device according to claim 1, wherein said high voltage generator is displaceable in a direction parallel to the longitudinal axis of the hollow body to be tested.

9. A device according to claim 1, further comprising means for supporting the hollow body to be tested.

10. A device according to claim 9, wherein said supporting means comprises a plurality of rollers.

11. A device according to claim 9, further comprising a crossbeam aligned with said supporting means, said crossbeam being positioned within said hollow body to be tested when said hollow body to be tested is supported by said supporting means.

12. A device according to claim 11, wherein said x-ray tube is disposed on a movable carriage, said movable carriage being linearly displaceable within the hollow body to be tested along a surface of said crossbeam.

13. A device according to claim 12, wherein said crossbeam is movable vertically relative to said support means, where the distance between said x-ray tube and an interior surface of the hollow body to be tested may be adjusted.

14. A device according to claim 1, wherein said high-voltage generator is displaceable vertically relative to the longitudinal axis of the hollow body to be tested.

* * * * *